US008575139B2

(12) United States Patent
Tuiten et al.

(10) Patent No.: US 8,575,139 B2
(45) Date of Patent: Nov. 5, 2013

(54) USE OF TESTOSTERONE AND A 5-HT1A AGONIST IN THE TREATMENT OF SEXUAL DYSFUNCTION

(75) Inventors: Jan Johan Adriaan Tuiten, Almere (NL); Johannes Martinus Maria Bloemers, Almere (NL); Robertus Petrus Johannes De Lange, Hilversum (NL)

(73) Assignee: Emotional Brain B.V., Almere (NL)

( * ) Notice: Subject to any disclaimer, the term of this patent is extended or adjusted under 35 U.S.C. 154(b) by 533 days.

(21) Appl. No.: 12/513,358

(22) PCT Filed: Nov. 2, 2007

(86) PCT No.: PCT/NL2007/050533
§ 371 (c)(1),
(2), (4) Date: Jan. 7, 2010

(87) PCT Pub. No.: WO2008/054213
PCT Pub. Date: May 8, 2008

(65) Prior Publication Data
US 2010/0160270 A1    Jun. 24, 2010

(30) Foreign Application Priority Data
Nov. 3, 2006   (EP) .................................... 06076976

(51) Int. Cl.
*A61K 31/56*      (2006.01)
*A61K 31/135*     (2006.01)

(52) U.S. Cl.
USPC ............................ 514/171; 514/656; 514/657

(58) Field of Classification Search
USPC ........................................ 514/171, 656, 657
See application file for complete search history.

(56) References Cited

U.S. PATENT DOCUMENTS

| | | | |
|---|---|---|---|
| 3,976,776 A | 8/1976 | Wu et al. | |
| 4,521,421 A * | 6/1985 | Foreman ....................... | 514/267 |
| 4,596,795 A | 6/1986 | Pitha | |
| 4,640,921 A | 2/1987 | Othmer et al. | |
| 4,833,142 A | 5/1989 | Hartog et al. | |
| 4,877,774 A | 10/1989 | Pitha et al. | |
| 5,015,646 A | 5/1991 | Simms | |
| 5,250,534 A | 10/1993 | Bell et al. | |
| 5,389,687 A | 2/1995 | Schaus et al. | |
| 5,565,466 A | 10/1996 | Gioco et al. | |
| 5,731,339 A | 3/1998 | Lowrey | |
| 5,877,216 A | 3/1999 | Place et al. | |
| 6,165,975 A | 12/2000 | Adams et al. | |
| 6,242,436 B1 | 6/2001 | Llewellyn | |
| 6,246,436 B1 | 6/2001 | Lin et al. | |
| 6,251,436 B1 | 6/2001 | Drizen et al. | |
| 6,294,550 B1 | 9/2001 | Place et al. | |
| 6,306,841 B1 | 10/2001 | Place et al. | |
| 6,423,683 B1 | 7/2002 | Heaton et al. | |
| 6,428,769 B1 | 8/2002 | Rubsamen et al. | |
| 6,469,012 B1 | 10/2002 | Ellis et al. | |
| 6,469,016 B1 | 10/2002 | Place et al. | |
| 6,472,434 B1 | 10/2002 | Place et al. | |
| 6,541,536 B2 | 4/2003 | Weikard et al. | |
| 6,608,065 B1 | 8/2003 | Daugan | |
| 6,610,652 B2 | 8/2003 | Adams et al. | |
| 6,632,419 B2 | 10/2003 | Rubsamen et al. | |
| 6,964,780 B1 | 11/2005 | King et al. | |
| 7,151,103 B2 * | 12/2006 | Borsini et al. ........... | 514/254.06 |
| 7,198,801 B2 | 4/2007 | Carrara et al. | |
| 2003/0022877 A1 | 1/2003 | Dudley | |
| 2003/0027804 A1 | 2/2003 | Van der Hoop | |
| 2003/0104980 A1 | 6/2003 | Borsini et al. | |
| 2004/0014761 A1 | 1/2004 | Place et al. | |
| 2004/0186086 A1 | 9/2004 | Bunschoten et al. | |
| 2004/0208829 A1 | 10/2004 | Rubsamen et al. | |
| 2005/0152956 A1 | 7/2005 | Dudley | |
| 2006/0040935 A1 | 2/2006 | Maytom et al. | |
| 2006/0270642 A1 | 11/2006 | Lehman et al. | |
| 2006/0281752 A1 | 12/2006 | Heaton et al. | |
| 2006/0287335 A1 | 12/2006 | Sukoff Rizzo et al. | |
| 2007/0093450 A1 | 4/2007 | Tuiten | |
| 2007/0149454 A1 | 6/2007 | Mattern | |
| 2007/0154533 A1 | 7/2007 | Dudley | |
| 2009/0306026 A1 | 12/2009 | Tuiten et al. | |
| 2010/0093680 A1 | 4/2010 | Tuiten et al. | |
| 2010/0152145 A1 | 6/2010 | Tuiten et al. | |
| 2010/0160270 A1 | 6/2010 | Tuiten et al. | |

FOREIGN PATENT DOCUMENTS

| | | |
|---|---|---|
| EP | 2000143 | 12/2008 |
| JP | 11-504902 | 5/1999 |
| JP | 2003-530430 | 10/2003 |
| JP | 2004-520320 | 7/2004 |
| NZ | 524601 | 4/2006 |
| RU | 2130776 | 5/1999 |
| RU | 97117167 | 10/1999 |
| RU | 2152787 | 7/2000 |
| RU | 2180591 | 3/2002 |
| RU | 2285519 | 10/2006 |

(Continued)

OTHER PUBLICATIONS

Rendell et al., JAMA, 1999;281(5):421-426.*
International Preliminary Report on Patentability for PCT/NL2007/050533, mailed on Jul. 2, 2009, 8 pages.
Fourcroy, Drugs (2003) 63:1445-1457.
Kuhn, Rec. Progress Hormone Research (2002) Academic Press vol. 57, pp. 411-434.
Shifren et al., New England Journal of Medicine (2000) 343:682-688.
Spungen et al., The Mount Sinai Journal of Medicine (1999) 66:201-205.
Traish et al., Drug Discovery Today: Disease Mechanisms (2004) 1(1):91-97.
International Search Report for PCT/NL2007/050533, mailed on Feb. 25, 2009, 3 pages.
Rasia-Filho et al., Hormones and Behavior (1996) 30(3):251-258.
Written Opinion of the International Searching Authority for PCT/NL2007/050533, issued on May 5, 2009, 5 pages.
Belikov et al. Pharmaceutical Chemistry (1993) 43-47 (machine translation provided).

(Continued)

*Primary Examiner* — San-Ming Hui
(74) *Attorney, Agent, or Firm* — Morrison & Foerster LLP

(57) ABSTRACT

The invention relates to the field of male and/or female sexual dysfunction. The invention specifically relates to the use of testosterone and a 5-HT1A agonist.

9 Claims, No Drawings

(56) References Cited

FOREIGN PATENT DOCUMENTS

| | | |
|---|---|---|
| WO | WO-94/28902 | 12/1994 |
| WO | WO-95/05188 | 2/1995 |
| WO | WO-95/33486 | 12/1995 |
| WO | WO-96/28142 | 9/1996 |
| WO | WO-96/33705 | 10/1996 |
| WO | WO-96/36339 | 11/1996 |
| WO | WO-97/03675 | 2/1997 |
| WO | WO-99/21562 | 5/1999 |
| WO | WO-99/62502 | 9/1999 |
| WO | WO-00/66084 | 11/2000 |
| WO | WO-01/78703 | 10/2001 |
| WO | WO-02/26214 | 4/2002 |
| WO | WO-02/051420 | 7/2002 |
| WO | WO-02/069906 | 9/2002 |
| WO | WO-03/011300 | 2/2003 |
| WO | WO-03/002123 | 9/2003 |
| WO | WO-2004/037173 | 5/2004 |
| WO | WO-2004/037262 | 5/2004 |
| WO | WO-2005/007166 | 1/2005 |
| WO | WO-2005/039530 | 5/2005 |
| WO | WO-2005/094827 | 10/2005 |
| WO | WO-2005/102342 | 11/2005 |
| WO | WO-2005/107810 | 11/2005 |
| WO | WO-2006/127057 | 11/2006 |
| WO | WO-2007/054791 | 5/2007 |
| WO | WO-2007/055563 | 5/2007 |

OTHER PUBLICATIONS

Berman et al., "Safety and Efficacy of Sildenafil Citrate for the Treatment of Female Sexual Arousal Disorder: A Double-Blind, Placebo Controlled Study," Journal of Urology (2003) 170(6):2333-2338.
Doggrell, "Comparison of Clinical Trials with Sildenafil, Vardenafil and Tadalafil in Erectile Dysfunction," Expert Opin. Pharmacother. (2005) 6(1):1-2. (abstract).
Dyson et al., "May's Chemistry of Synthetic Drugs," ($5^{th}$ ed. 1959) (machine translation provided).
Frye et al., "Behavioral Effects of 3 Alpha-Androstanediol.1: Modulation of Sexual Receptivity and Promotion of GABA-Stimulated Chloride Flux," Behav. Brain Res. (1996) 79 (1-2):109-118. (abstract).
Graham-Smith et al., Oxford Handbook of Clinical Pharmacology and Pharmacotherapy (2000) 18-20 (machine translation provided).
Haensel et al., "Flesinoxan: A Prosexual Drug for Male Rats," European Journal of Pharmacology (1997) 330:1-9.
Kharkevich et al. Pharmacology ($3^{rd}$ ed. 1987) 41-42 (machine translation provided).
Koolman et al., Biochemistry (1998) 365 (machine translation provided).
Morali et al., (1994) "Mechanisms Regulating Male Sexual Behavior in the Rat: Role of $3\alpha$-and $3\beta$-Androstanediols," Biology of Reproduction 51:562-571.
Phillips, "Female Sexual Dysfunction: Evaluation and Treatment," Am Fam Physician (2000) 62(1): 127-136, 141-142.
Rendell et al., "Sildenafil for Treatment of Erectile Dysfunction in Men with Diabetes A Randomized Controlled Trial," JAMA (1999) 281(5):421-426.
Sher et al., "Vaginal Sildenafil (Viagra): A Preliminary Report of a Novel Method to Improve Uterine Artery Blood Flow and Endometrial Development in Patients Undergoing IVF," Human Reproduction (2000) 15(4):806-809.
Shields et al., "Use of Sildenafil for Female Sexual Dysfunction," Ann. Pharmacother. (2006) 40:931-934.
Singh et al. (2006) "Pharmokinetics of a Testosterone Gel in Healthy Postmenopausal Women," The Journal of Clinical Endocrinology & Metabolism 91(1):136-144.
The Merck Manual of Diagnosis and Therapy 30-36 (Robert Berkow, M.D. et al. eds., Merck Research Laboratories, Merck & Co., Inc. 1992) (1997) (machine translation provided).
The RLS Encyclopedia of Drugs, RLS 2004, vol. 11 (machine translation provided).
Tuiten et al., "Time Course of Effects of Testosterone Administration on Sexual Arousal in Women," Arch. Gen. Psychiatry (2000) 57:149-153.
Vidal's Handbook, Drugs in Russia, Moscow AstraPharmService 2001 (machine translation provided).
International Search Report for International Patent Application No. PCT/NL2005/000355, mailed Dec. 18, 2006, 5 pages.
International Search Report for International Patent Application No. PCT/NL2006/000542, mailed Jul. 17, 2007, 5 pages.
International Preliminary Report on Patentability for International Patent Application No. PCT/NO2007/050534, mailed Jul. 2, 2009, 8 pages.
International Search Report for International Patent Application No. PCT/NO2007/050534, mailed Feb. 24, 2009, 3 pages.
International Preliminary Report on Patentability for International Patent Application No. PCT/NO2007/050535, mailed Jul. 2, 2009, 9 pages.
International Search Report for International Patent Application No. PCT/NO2007/050535, mailed Feb. 24, 2009, 3 pages.

* cited by examiner

USE OF TESTOSTERONE AND A 5-HT1A AGONIST IN THE TREATMENT OF SEXUAL DYSFUNCTION

CROSS-REFERENCE TO RELATED APPLICATIONS

This application is the national phase of PCT/NL2007/050533 having an International filing date of 2 Nov. 2007, which claims benefit of European patent application No. 06076976.7 filed 3 Nov. 2006. The contents of the above patent applications are incorporated by reference herein in their entirety.

The invention relates to the field of male and/or female sexual dysfunction. The invention specifically relates to the use of testosterone and a 5-HT1A agonist, optionally in combination with a PDE5 inhibitor.

Male Sexual Dysfunction (MSD) refers to various disturbances or impairments of male sexual function, including inhibited sexual desire (ISD), erectile dysfunction (ED) or impotence and premature ejaculation (PE, also known as rapid ejaculation, early ejaculation, or ejaculatio praecox) and anorgasmia. ED is treated successfully using PDE5 inhibitors such as sildenafil, vardenafil and tadalafil. Current successful treatment for PE includes anaesthetic creams (like lidocaine, prilocaine and combinations) that reduce sensation on the penis and SSRI antidepressants such as paroxetine, fluoxetine and sertraline. There is currently no known successful medication for ISD.

Female Sexual Dysfunction (FSD) refers to various disturbances or impairments of sexual function, including a lack of interest in sexual activity, repeated failure to attain or maintain sexual excitement, inability to attain an orgasm following sufficient arousal. A recent study estimated that 43% of women suffer from sexual dysfunction in the USA[1]. Low sexual desire (22% prevalence) and sexual arousal problems (14% prevalence) belong to the most common categories of sexual dysfunction of women. These categories are convenient in providing working definitions and an accepted lexicon for researchers and therapists. However, it may be incorrect to assume that these disorders are fully independent of each other. Both case studies and epidemiological studies demonstrate that these disorders can overlap and may be interdependent. In some cases, it may be possible to identify the primary disorder that led to the others, but in many cases, this may be impossible.

For the treatment of male and/or female sexual disorder (or dysfunction) a number of different treatments, with greater or lesser degrees of success have been suggested and applied. For example, WO 2005/107810 describes the use of testosterone and a type 5 phosphodiesterase (PDE5) inhibitor which components must be released within a certain order and timeframe in respect of sexual activity. Although this treatment provides promising results, there is a need for alternative treatments.

In one of its embodiments, the invention provides use of testosterone and a 5-HT1A agonist in the preparation of a medicament for the treatment of sexual dysfunction, wherein said 5-HT1A is essentially released one hour before and said testosterone 3.5-5.5 hours prior to sexual activity. In a preferred embodiment said testosterone is sublingual testosterone.

Testosterone is also known under the chemical name 17-β-hydroxyandrost-4-en-3-one which can be obtained in various ways: it may be isolated and purified from nature or synthetically produced by any manner. Besides testosterone also an "analogue of testosterone" can be used. The term "or analogue thereof" includes any useful metabolite or precursor of testosterone, for example the metabolite dihydrotestosterone. It is clear to the skilled person that if a metabolite or precursor of testosterone is used, the time point for administration of for example a 5-HT1a agonist (and optionally also a PDE5 inhibitor) needs to be reconsidered. If, for example, dihydrotestosterone is used, the time of administration of a 5-HT1a agonist lies approximately half an hour earlier (as this is the approximate time it takes for excess testosterone to be converted to dihydrotestosterone).

According to the invention the level of free testosterone should be a peak plasma level of free testosterone of about at least 0,010 nmol/L, which will typically occur between 1 and 20 minutes after administration of the testosterone. About three and a half to five and a half hours after this plasma testosterone peak, there is a testosterone effect peak, i.e. there is a time lag in the effect of testosterone on genital arousal in sexually functional women.

Testosterone is preferably given in a formulation wherein there is a short-lasting high peak of testosterone in the blood circulation of the subject to whom it is administered. The invention therefore provides a use, wherein the testosterone or an analogue thereof is provided in the form of a sublingual formulation, such as a sublingual formulation comprising cyclodextrins as carrier. Another example of a suitable route of administration is buco-mucosally or intranasally, which can also be performed with the use of a cyclodextrin formulation or other usual excipients, diluents and the like. A typical example of a formulation is given in hydroxypropyl-beta cyclodextrin, but other beta cyclodextrins and other usual excipients, diluents and the like are within the skill of the art for preparing a formulation comprising testosterone or an analogue thereof, which releases essentially all of the testosterone within one short burst. Said burst will typically be within a short time interval (for example within 60-120 seconds, more preferably within 60 seconds) upon administration, leading to blood peak levels of testosterone about 1-20 minutes later. In a preferred embodiment, the pharmaceutical is designed for sublingual administration and even more preferred said composition comprises cyclodextrin such as hydroxypropyl-beta cyclodextrin. A typical example of a prepared testosterone sample (for 0.5 mg of testosterone) consists of 0.5 mg testosterone, 5 mg hydroxypropyl-betacyclodextrines (carrier), 5 mg ethanol, and 5 ml water, but each of the amounts of these substances might be higher or lower.

Testosterone in the circulation is typically bound by SHBG (steroid hormone binding globulin) and by albumin. It is important that the peak plasma level of testosterone as defined in the present invention is present and calculated as free testosterone, so a fraction not bound by albumin and SHBG. Thus the dose of testosterone given should be high enough to saturate the albumin and SHBG (i.e. the concentration of testosterone must be high enough to overcome complete binding of testosterone by SHBG or albumin), or another way of avoiding binding to albumin or SHBG must be designed, such as the use of a competitor for the testosterone binding site on SHBG.

In contrast to other sexual dysfunction treatments based on testosterone, the use (and method) described herein aim at a temporary increase in the testosterone level in the treated subject. Most other methods aim at restoring/replacing/replenishing of the testosterone level to normal (i.e. physiological) levels (as found in a normal subject). In a preferred embodiment, testosterone is applied such that a short-lasting high peak of testosterone in the blood circulation of the subject to whom it is administered, is obtained. The term "short-lasting" refers to an application of testosterone such that the blood serum testosterone levels are back to base-line level within 2 hours after administration.

Preferably, the used 5-HT1A agonist is selective for the 5-HT1A receptor over other 5-HT receptors and the α-adrenoreceptor and dopamine receptor. Non-limiting examples of a 5-HT1A agonist are 8-OH-DPAT, Alnespirone, AP-521, Buspar, Buspirone, Dippropyl-5-CT, DU-125530, E6265, Ebalzotan, Eptapirone, Flesinoxan, Flibanserin, Gepirone, Ipsapirone, Lesopitron, LY293284, LY301317, MKC242, R(+)-UH-301, Repinotan, SR57746A, Sunepitron, SUN-N4057, Tandosporine, U-92016A, Urapidil, VML-670, Zalospirone or Zaprasidone.

The application of a 5-HT1a agonist is such that, just as the testosterone, there is a peak present within the blood. In a preferred embodiment, the used 5-HT1a agonist is applied such that there is a peak within the blood around 4 hours after the (burst release) administration of testosterone.

The application of testosterone as well as a 5-HT1a agonist is acute, i.e. on demand, and not chronic. In other words, the administration of testosterone and/or a 5-HT1a agonist is only done just before sexual activity, compared to a chronic dosing regime/situation/application that aims at restoring the levels to physiological levels.

Reference herein to sexual dysfunction includes male and/or female dysfunction. Reference to male sexual dysfunction includes inhibited sexual desire (ISD), erectile dysfunction (ED) and premature ejaculation (PE).

Reference to female sexual dysfunction includes Hypoactive Sexual Desire Disorder (HSDD), Female Sexual Arousal Disorder (FSAD) and Female Orgasmic Disorder (FOD).

Without being bound by it, the inventors provide the following explanation for the treatment of sexual dysfunction by providing a subject in need thereof with testosterone and a 5-HT1a agonist. Testosterone makes the brain more receptive for sexual cues and increases subjective sexual arousal. To prevent humans from acting upon such arousal in situations where this is deemed inappropriate, the prefrontal cortex can inhibit automated/reflexive responses, thereby also inhibiting physical sexual arousal. We pose that women with FSD, in particular women with FSAD, suffer from exaggerated inhibitory action of the prefrontal cortex, which is relieved (inhibition-of-inhibition) by using a 5-HT1A agonist.

The embodiments referring to a 5-HT1A agonist are preferably used to treat female sexual dysfunction, i.e. to improve subjective and physical sexual arousal (female sexual arousal disorder) and is especially effective in women suffering from female sexual arousal disorder, by disinhibiting the brain's inhibition of sexual behaviour.

In a preferred embodiment, the invention provides use of testosterone and a 5-HT1A agonist in the preparation of a medicament for the treatment of female sexual dysfunction, wherein said 5-HT1A is essentially released one hour before and said testosterone 3.5-5.5 hours prior to sexual activity. In yet another preferred embodiment, the invention provides use of testosterone, a PDE5 inhibitor and a HT1A agonist in the preparation of a medicament for the treatment of female sexual dysfunction, wherein said 5-HT1A is essentially released one hour before, said PDE5 inhibitor 1-2 hours and said testosterone 3.5-5.5 hours prior to sexual activity. Preferably said female sexual dysfunction is female sexual arousal disorder (FSAD).

In yet another preferred embodiment, said sexual dysfunction is male sexual dysfunction.

It is clear, that preferably the (peak) effect of a 5-HT1a agonist as well as the (peak) effect of testosterone coincide (completely). It is however noted that if the peak effect of testosterone and of a 5-HT1a agonist only partly overlap this still results in the desired effect. When the testosterone is provided such that it essentially releases all of the testosterone within one short burst to a (for example female) subject, a 5-HT1a agonist is preferably provided such that it results in a peak plasma concentration at least 3 hours after the administration of testosterone. Even more preferred, the 5-HT1a agonist effect is present 3.5-5.5 hours after the intake of testosterone. It is clear that the exact time of the 5-HT1a agonist administration is dependent on the type of formulation used. If the 5-HT1a agonist formulation is released shortly after administration, it is of no use to provide it at the same time as the testosterone is provided, because there will be hardly any overlap of effect. If it takes some time before the 5-HT1a agonist is available from the used formulation, for example 3.5 to 4.5 hours, it can be/is administrated at the same time the testosterone is administered.

Without being bound by theory, the experimental part herein describes the inventor's current hypothesis in respect of the effect of a 5-HT1a agonist in the treatment of sexual dysfunction.

In yet another embodiment, the invention provides use of testosterone, a PDE5 inhibitor and a 5-HT1A agonist in the preparation of a medicament for the treatment of sexual dysfunction, wherein said 5-HT1A is essentially released one hour, said PDE5 inhibitor 1-2 hours and said testosterone 3.5-5.5 hours prior to sexual activity. In a preferred embodiment said testosterone is sublingual testosterone.

Multiple PDE5 inhibitors are available. An example of a PDE5 inhibitor is vardenafil HCl which is designated chemically as piperazine, 1-[[3-(1,4-dihydro-5-methyl-4-oxo-7-propylimidazo[5,1-f][1,2,4]triazin-2-yl)-4-ethoxyphenyl]sulfonyl]-4-ethyl-, monohydrochloride. In addition to the active ingredient, vardenafil HCl, each tablet contains microcrystalline cellulose, crospovidone, colloidal silicon dioxide, magnesium stearate, hypromellose, polyethylene glycol, titanium dioxide, yellow ferric oxide, and red ferric oxide. Another example is given in sildenafil citrate which is chemically designated as 1-[[3-(6,7-dihydro-1-methyl-7-oxo-3-propyl-1Hpyrazolo[4,3-d]pyrimidin-5-yl)-4-ethoxyphenyl]sulfonyl]-4-methylpiperazine citrate. In addition to the active ingredient, sildenafil citrate, each tablet contains the following ingredients: microcrystalline cellulose, anhydrous dibasic calcium phosphate, croscarmellose sodium, magnesium stearate, hydroxypropyl methylcellulose, titanium dioxide, lactose, triacetin, and FD & C Blue #2 aluminum lake. Another example is given in tadalafil which is chemically designated as pyrazino[1',2':1,6]pyrido[3,4-b]indole-1,4-dione, 6-(1,3-benzodioxol-5-yl)-2,3,6,7,12,12a-hexahydro-2-methyl-, (6R,12aR)-. In addition to the active ingredient, tadalafil, each tablet contains the following ingredients: croscarmellose sodium, hydroxypropyl cellulose, hypromellose, iron oxide, lactose monohydrate, magnesium stearate, microcrystalline cellulose, sodium lauryl sulfate, talc, titanium dioxide, and triacetin.

The number of PDE5-inhibitors is still expanding and other non-limiting examples are: E-4021, E-8010, E-4010, AWD-12-217 (zaprinast), AWD 12-210, UK-343,664, UK-369003, UK-357903, BMS-341400, BMS-223131, FR226807, FR-229934, EMR-6203, Sch-51866, IC485, TA-1790, DA-8159, NCX-911 or KS-505a or the compounds disclosed in WO 96/26940.

It is clear to the skilled person that the active ingredients are preferably administrated/released such that their peak effects (i.e. their activities) at least partly overlap/coincide and preferably completely overlap. In respect of testosterone the peak effect means the maximal increase in attention to erotic stimuli and in sexual motivation. For a PDE5 inhibitor the peak effect is the maximal increase in activity of the NANC (non adrenergic non cholinergic) pathway of the autonomous nervous system and in respect of a 5-HT1A agonist this means a maximal behavioural disinhibition. This goal can be reached by using different strategies.

As outlined above, for an optimal effect of testosterone, a 5HT1a agonist and a PDE5 inhibitor, it is desired that the peak effect of said compounds coincide. However, even if the peak effects only overlap partly, this still results in the desired effect (for example, treatment of FSD). There is a time lag for the effect of a 5-HT1a agonist of about 1 hour and the effect of a 5-HT1a agonist lasts for several hours (for example, Flesinoxan reaches maximum plasma concentration after 1-2 hours, and single doses have a half-life of 5.5 hours). PDE5-inhibitors such as vardenafil and sildenafil typically reach their peak plasma concentration (which should be at least 35 ng/ml for sildenafil, 2 µg/l for vardenafil and 40 µgl for tadalafil) after about 1 hour after administration and their effect is then also present. By releasing a 5-HT1a agonist and a PDE5 inhibitor at approximately the same time, their effects at least partly coincide. It is clear to the skilled person that a 5-HT1a agonist and a PDE5 inhibitor can be formulated such that their release is delayed. For example, the active ingredients are provided with or surrounded by a coating, which is dissolved after 2 hours. In such a case, the active ingredients must be taken 1.5-3.5 hours before sexual activity. Other variations are easily performed by the skilled person and are within the scope of the present invention.

For the present invention the routes of administration of choice are those which are the least invasive (for example oral, buco-mucosal or intranasal). Motivation for sexual behaviour should not be negatively influenced by invasive routes of administration.

The use as described herein may alternatively be formulated as:
(i) testosterone and a 5-HT1a agonist for use in a method for treating sexual dysfunction; or
(ii) testosterone, a PDE5-inhibitor and a 5-HT1a agonist for use in a method for treating sexual dysfunction.

The invention further provides a pharmaceutical composition comprising testosterone and a 5-HT1A agonist, wherein said formulation is designed to essentially release said 5-HT1A one hour and said testosterone 3.5-5.5 hours prior to sexual activity.

The amount of testosterone per pharmaceutical composition comprising testosterone is at least 0.3 mg testosterone and at most 2.5 mg testosterone. Higher or lower doses may be necessary depending on the albumin and SHBG levels and the weight of the subject to be treated. The suitable amount of 5-HT1a agonist depends on the used 5-HT1a agonist as well as on for example the weight of the patient. Flexinoxan for example is typically provided in an amount of 1 mg.

The invention also provides a pharmaceutical composition comprising testosterone, a PDE5 inhibitor and a 5-HT1A agonist, wherein said formulation is designed to essentially release said 5-HT1A one hour, said PDE5 inhibitor 1-2 hours and said testosterone 3.5-5.5 hours prior to sexual activity. One suitable amount of a 5-HT1A agonist is approximately 1 mg. An advantage of using at least three different active ingredients is that the individual used amounts may be decreased if compared to a treatment based on two active ingredients.

The active ingredients (for example testosterone, a PDE5 inhibitor or a 5-HT1A agonist) may be present in any suitable form, such as in the form of tablets, capsules, multi-particulates, gels, films, solutions or suspensions and may comprise diluents and/or excipients and/or binders and/or disintegrants and/or lubricants and/or colouring agents. Also different kinds of release patterns can be applied, such as direct release or delayed release.

Because the effects of the different active ingredients must at least partly coincide and preferably completely coincide, the invention preferably also provides instructions as to the administration. Therefore, the invention also provides a kit of parts comprising at least one pharmaceutical composition comprising testosterone and at least one composition comprising a 5-HT1A agonist, wherein said kit further comprises instructions in respect to the administration of said compositions. In yet another embodiment, the invention also provides a kit of parts comprising at least one pharmaceutical composition comprising testosterone, at least one composition comprising a PDE5 inhibitor and at least one composition comprising a 5-HT1A agonist, wherein said kit further comprises instructions in respect to the administration of said compositions.

It should be clear that depending on the formulation of the different active ingredients, different administration regimes can be used.

In order to further enhance the effects of the kit of parts of the invention said kit may further comprise means for cognitive interventions and stimulation. Such information may be present on any data carrier (paper, CD, DVD), passive or interactive, or it may be a link to a website at least partially designed for the purpose of said cognitive stimulation. Sometimes it is preferred to present said cognitive stimulatory information subconsciously e.g. subliminally.

The herein described combinations of active ingredients may further be accompanied by other suitable active ingredients.

The invention further provides a method for treating a male or a female suffering from sexual dysfunction by providing to said male or female with a combination of testosterone and a 5-HT1A agonist (and optionally a PDE5-inhibitor).

The invention will be explained in more detail in the following, non-limiting examples.

EXPERIMENTAL PART

Case Reports on Combined Testosterone and Buspirone Medication for FSD
Rationale A number of women who had participated in our FSD-medication trials had reported strong feelings of inhibition whilst contemplating or having sexual intercourse. Three of these women were prescribed a single dose of testosterone (T) combined with a single dose of Buspirone (B), by a qualified physician, in a laboratory setting. T is known to make the brain more perceptive to sexual stimuli, B was given for its 5-HT1A receptor agonism, to reduce said inhibition.
Set-Up All women were given Placebo or T/B medication randomly and on separate days. T (0.5 mg, suspension, sublingually) was given 4 hours and B (5 mg, tablet, orally) was given 1.5 hours prior to measurements. Physical arousal was measured using Clitoral Blood Volume (CBV) measurements; subjective sexual arousal was measured using the Sexual Arousal Response Self-Assessment Questionnaire (SARSAQ). In addition, Vaginal Pulse Amplitude (VPA) was measured as a measure for physical anticipation of sexual activity. CBV and VPA were measured during neutral filmclips, and subsequent erotic filmclips. Each session of neutral and erotic filmclips was followed by a SARSAQ. The erotic film clips were progressively more explicit during subsequent (total of four) sessions. The results below are described as the overall relative increase in physical arousal (CBV and VPA, in percent points) and subjective sexual arousal (SARSAQ, in Likert scale points) during the erotic filmclips under placebo and T/B condition.

Case A

This woman was diagnosed with both Hypo Sexual Desire Disorder (HSDD, DSM-IV TR inclusion criteria) and Female Sexual Arousal Disorder (FSAD, DSM-IV TR inclusion criteria). She feels sexually inhibited, which is only released when she's had too much to drink. She interprets compliments about her looks as direct invitation for sex which immediately results in feelings of inhibition.

Average SARSAQ increase was 0.44 points, peaking at 0.9 points during the third session neutral/erotic film clips. Average increase in VPA was 1.3 points, peaking at 3.9 during the second session. Average increase in CBV was 10.2 peaking at 12.6 during the third session.

Case B

This woman was also diagnosed with both HSDD and FSAD. She says she's lost the desire for sex she used to have and finds it very difficult to unwind and is very easily distracted, causing her not to become physically aroused. Average SARSAQ increase was 2.03 points, peaking at 6.23 points during the second session neutral/erotic film clips. Average increase in VPA was −0.4 points, peaking at −0.0 during the first session. Average increase in CBV was 4.0 peaking at 5.8 during the first session.

Case C

Case C suffers from HSDD but not from FSAD. She puts much effort into trying to regain desire for sex, but is often put-off by her partner who she claims is overly clingy.

Average SARSAQ increase was −0.44 points, peaking at 0.01 points during the first session neutral/erotic film clips. She did report to the physician that she felt more sexually aroused during verum. Average increase in VPA was 0.3 points, peaking at 0.3 during the first session. Average increase in CBV was 17.5 peaking at 19.3 during the first session.

Overall Conclusion

Combined treatment with T/B increased physical sexual arousal (CBV) over placebo, in all three cases. Physical anticipation of sexual activity (VPA) was increased in two out of three cases. Together, these measurements indicate a major improvement in physical sexual arousal. CBV was increased in both FSAD patients, VPA in one out of two.

Subjective sexual arousal, measured by SARSAQ, was increased in two out of three cases, both combined HSDD and FSAD patients. Although the SARSAQ scores of case C did not increase, she did report feeling more sexually aroused during verum.

We expect to further improve these results by using full as opposed to partial 5-HT1A receptor agonists (flesinoxan instead of buspirone), by varying the dose of 5-HT1A receptor agonist and by combining T/B treatment with PDE5 inhibitors.

Experiment 1 testosterone and flesinoxan in FSD

Efficacy of combined administration of testosterone and a 5-HT1A receptor agonist—flesinoxan—on VPA in response to erotic film excerpts in women with FSD In a double-blind, randomly assigned placebo controlled cross-over design, a group of 16 women with female sexual dysfunction (FSD) will receive
1. testosterone (0.5 mg) and flesinoxan (1 mg)
2. testosterone (0.5 mg) alone
3. flesinoxan (1 mg) alone
4. placebo
on 4 separate experimental days.

The four experimental days will be separated by (at least) a three-day period. On all drug administrations, subjects will receive one capsule consisting of either flesinoxan, or a placebo, and one liquid formulation with either testosterone or placebo. The vaginal pulse amplitude will be measured in response to neutral and erotic film excerpts, directly after administration of liquid formulation, and 4 hours after administration of liquid formulation. Thus, the liquid formulation will be taken four hours prior to testing, the capsule one hour prior to testing. The effect of sublingual testosterone and flesinoxan will overlap due to their different time lag (3.5-4.5 hours and 0-1 hour, respectively).

Experiment 2 testosterone, flesinoxan and sildenafil in FSD

Efficacy of combined administration of testosterone, a 5-HT1A receptor agonist—flesinoxan- and PDE5 inhibitor—sildenafil—on VPA in response to erotic film excerpts in women with FSD In a double-blind, randomly assigned placebo controlled cross-over design, a group of 16 women with female sexual dysfunction (FSD) will receive
1. testosterone (0.5 mg), flesinoxan (1 mg) and sildenafil (10 mg)
2. testosterone (0.5 mg) and flesinoxan (1 mg)
3. flesinoxan (1 mg) and sildenafil (10 mg)
4. testosterone (0.5 mg) alone
5. flesinoxan (1 mg) alone
6. placebo
on 6 separate experimental days.

The six experimental days will be separated by (at least) a three-day period. On all drug administrations, subjects will receive one capsule consisting of either flesinoxan, and/or sildenafil or a placebo, and one liquid formulation with either testosterone or placebo. The vaginal pulse amplitude will be measured in response to neutral and erotic film excerpts, directly after administration of liquid formulation, and 4 hours after administration of liquid formulation. Thus, the liquid formulation will be taken four hours prior to testing, the capsule one hour prior to testing. The effect of sublingual testosterone, flesinoxan and sildenafil, will overlap due to their different time lags (3.5-4.5 hours, 0-1 hour and 0-1 hour, respectively).

During the experimental sessions of experiments 1-2, the subject must insert a tampon-shaped vaginal probe (a photoplethysmograph) in order to measure the VPA. Then subjects will view a 10 minute neutral fragment, followed by a 5 minute erotic film fragment. After these baseline measurements, the subjects receive one of the four medication combinations as described above. Following medication another set of neutral (5 minutes) and erotic (5 minutes) film fragments is shown. The vaginal probe will then be removed. After 4 hours another VPA measurement will be made in response to neutral (5 minutes) and erotic (5 minutes) film fragments. Blood pressure (supine and standing), heart rate, respiration rate, and body temperature will be monitored throughout on the experimental days.

The experimental session will be preceded by a screening visit. In this screening visit subjects are interviewed and examined by a resident of the department of gynaecology of Flevo Hospital, Almere to diagnose for FSD and to determine eligibility for study participation. Subjects will be asked to fill out a questionnaire; the Female Sexual Function Index (FSFI). Subjects will be screened to exclude pregnancy or breast feeding, vaginal infections, major operations to the vagina and/or vulva, undetected major gynaecological illnesses or unexplained gynaecological complaints. Weight, height, blood pressure (supine and standing) will be measured. Cardiovascular condition will be tested and ECG checked for significant abnormalities.

Subjects with a history of endocrinological, neurological or psychiatric illness and/or treatment. Standard blood chemistry and hematology tests will be performed. Participants are required not to use alcohol or psychoactive drugs the evening before and the day of experimentation. During period of menstruation, subjects will not be tested.

Experiment 3 testosterone and flesinoxan in MSD

Efficacy of combined administration of testosterone and a 5-HT1A receptor agonist—flesinoxan—on male sexual function in response to erotic film excerpts in men with MSD In a double-blind, randomly assigned placebo controlled cross-over design, a group of 16 men with male sexual dysfunction (MSD) will receive
1. testosterone (0.5 mg) and flesinoxan (1 mg)
2. testosterone (0.5 mg) alone
3. flesinoxan (1 mg) alone
4. placebo on 4 separate experimental days.

The penile tumescence and rigidity will be measured in response to neutral and erotic film audiovisual stimulation (VSTR), directly after drug administration, and 1 hour after drug administration, directly followed by measurement of vibrotactile stimulation ejaculatory latency time (VTS-ELT) and postejaculatory erectile refractory time. The four experimental days will be separated by (at least) a three-day period. On all drug administrations, subjects will receive one capsule consisting of either flesinoxan, or a placebo, and one liquid formulation with either testosterone or placebo. The VSTR will be measured in response to neutral and erotic film excerpts, directly after administration of liquid formulation, and 4 hours after administration of liquid formulation, when also the VTS-ELT is measured. Thus, the liquid formulation will be taken four hours prior to testing, the capsule one hour prior to testing. The effect of sublingual testosterone and flesinoxan will overlap due to their different time lag (3.5-4.5 hours and 0-1 hour, respectively).

Experiment 4 testosterone, flesinoxan and sildenafil in MSD

Efficacy of combined administration of testosterone, a 5-HT1A receptor agonist—flesinoxan- and PDE5 inhibitor—sildenafil—on male sexual function in response to erotic film excerpts in men with MSD In a double-blind, randomly assigned placebo controlled cross-over design, a group of 16 men with male sexual dysfunction (MSD) will receive
1. testosterone (0.5 mg), flesinoxan (1 mg) and sildenafil (10 mg)
2. testosterone (0.5 mg) and flesinoxan (1 mg)
3. flesinoxan (1 mg) and sildenafil (10 mg)
4. testosterone (0.5 mg) alone
5. flesinoxan (1 mg) alone
6. placebo on 6 separate experimental days.

The penile tumescence and rigidity will be measured in response to neutral and erotic film audiovisual stimulation (VSTR), directly after drug administration, and 1 hour after drug administration, directly followed by measurement of vibrotactile stimulation ejaculatory latency time (VTS-ELT) and postejaculatory erectile refractory time. The six experimental days will be separated by (at least) a three-day period. On all drug administrations, subjects will receive one capsule consisting of either flesinoxan, or a placebo, and one liquid formulation with either testosterone or placebo. The VSTR will be measured in response to neutral and erotic film excerpts, directly after administration of liquid formulation, and 4 hours after administration of liquid formulation, when also the VTS-ELT is measured. Thus, the liquid formulation will be taken four hours prior to testing, the capsule one hour prior to testing. The effect of sublingual testosterone, flesinoxan and sildenafil, will overlap due to their different time lags (3.5-4.5 hours, 0-1 hour and 0-1 hour, respectively).

Experiments 3-4 will be preceded by a screening visit. In this screening visit subjects are interviewed and examined by a resident of the department of gynaecology of Flevo Hospital, Almere to diagnose for MSD and to determine eligibility for study participation. Subjects will be asked to fill out a questionnaire; the international index of erectile function questionnaire (IIEF). Weight, height, blood pressure (supine and standing) will be measured. Cardiovascular condition will be tested and ECG checked for significant abnormalities. Participants are required not to use alcohol or psychoactive drugs the evening before and the day of experimentation.

References

1. Laumann, E. O., A. Paik, and R. C. Rosen, *Sexual dysfunction in the United States: prevalence and predictors*. Jama, 1999. 281(6): p. 537-44.
2. Wudy, S. A., et al., *Androgen metabolism assessment by routine gas chromatography/mass spectrometry profiling of plasma steroids: Part 1, Unconjugated steroids*. Steroids, 1992. 57(7): p. 319-24.

The invention claimed is:

1. A method to treat sexual dysfunction in a subject in anticipation of sexual activity which method comprises acute administration on demand to said subject testosterone or an analog which is a precursor or metabolite thereof and a 5-HT1A agonist, wherein said testosterone or analog is released 3.5-5.5 hours prior to sexual activity such that a short lasting, high peak of testosterone or analog is reached in the blood circulation of said subject and said 5-HT1A agonist is provided such that the peak effects of the 5-HT1A agonist and testosterone or analog at least partly overlap.

2. The method of claim 1, wherein said sexual dysfunction is female sexual dysfunction.

3. The method of claim 1, wherein said sexual dysfunction is male sexual dysfunction.

4. The method of claim 1, wherein said 5-HT1A agonist is released one hour before sexual activity.

5. The method of claim 1 which employs a testosterone analog, which analog is dihydrotestosterone and wherein the 5-HT1A agonist is released 1-1.5 hours before sexual activity.

6. The method of claim 1 which employs testosterone.

7. The method of claim 6 wherein the 5-HT1A agonist is provided such that the peak plasma concentration of said agonist occurs at least three hours after the administration of testosterone.

8. The method of claim 6 wherein the 5-HT1A is released about 1-1.5 hours before sexual activity.

9. The method of claim 1 wherein the 5-HT1A agonist is selective for the 5-HT1A receptor over other 5-HT receptors, the alpha adrenoreceptor and the dopamine receptor.

* * * * *

UNITED STATES PATENT AND TRADEMARK OFFICE
CERTIFICATE OF CORRECTION

| | | |
|---|---|---|
| PATENT NO. | : 8,575,139 B2 | Page 1 of 1 |
| APPLICATION NO. | : 12/513358 | |
| DATED | : November 5, 2013 | |
| INVENTOR(S) | : Tuiten et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 887 days.

Signed and Sealed this
Fourteenth Day of July, 2015

Michelle K. Lee
*Director of the United States Patent and Trademark Office*